(12) United States Patent
Moberg-Alehammar et al.

(10) Patent No.: US 7,749,208 B2
(45) Date of Patent: Jul. 6, 2010

(54) INSERT FOR ABSORBENT ARTICLE HAVING A FECES RETAINING LAYER AND SPACER ELEMENT

(75) Inventors: Barbro Moberg-Alehammar, Mölndal (SE); Anna-Gerd Doverbo, Mölndal (SE)

(73) Assignee: SCA Hygiene Products AB, Gothenburg (SE)

( * ) Notice: Subject to any disclaimer, the term of this patent is extended or adjusted under 35 U.S.C. 154(b) by 429 days.

(21) Appl. No.: 10/392,895

(22) Filed: Mar. 21, 2003

(65) Prior Publication Data

US 2004/0019337 A1    Jan. 29, 2004

Related U.S. Application Data

(60) Provisional application No. 60/365,818, filed on Mar. 21, 2002.

(51) Int. Cl.
*A61F 13/15* (2006.01)
*A61F 13/20* (2006.01)

(52) U.S. Cl. .............. 604/385.19; 604/385.01; 604/385.06; 604/385.101; 604/385.12; 604/385.14; 604/385.13; 604/369; 604/378

(58) Field of Classification Search ........... 604/385.01, 604/385.06, 385.101, 385.12, 385.14, 378, 604/369, 379, 385.19, 385.03
See application file for complete search history.

(56) References Cited

U.S. PATENT DOCUMENTS

| | | | | |
|---|---|---|---|---|
| 4,554,297 A | * | 11/1985 | Dabi | 521/178 |
| 4,758,466 A | * | 7/1988 | Dabi et al. | 442/338 |
| 5,019,064 A | * | 5/1991 | Eilender | 604/378 |
| 5,171,236 A | * | 12/1992 | Dreier et al. | 604/369 |
| 5,405,342 A | * | 4/1995 | Roessler et al. | 604/364 |
| 5,514,121 A | * | 5/1996 | Roe et al. | 604/385.19 |
| 5,582,604 A | * | 12/1996 | Ahr et al. | 604/385.12 |
| 5,599,337 A | * | 2/1997 | Mccoy | 604/385.01 |
| 5,643,241 A | * | 7/1997 | Ahr et al. | 604/385.12 |
| 6,018,093 A | | 1/2000 | Roe et al. | |
| 6,133,501 A | * | 10/2000 | Hallock et al. | 604/369 |
| 6,168,584 B1 | * | 1/2001 | Allen et al. | 604/385.19 |
| 6,186,991 B1 | * | 2/2001 | Roe et al. | 604/361 |

(Continued)

FOREIGN PATENT DOCUMENTS

EP    0 464 855 A1    1/1992

(Continued)

OTHER PUBLICATIONS

Swedish Examiner Report dated Oct. 28, 2002.
PCT International Search Report dated May 28, 2003.
An English Translation of Notice of Reasons for Rejection in JP 2003-577760 dated Oct. 14, 2008.

*Primary Examiner*—Tatyana Zalukaeva
*Assistant Examiner*—Ginger T Chapman
(74) *Attorney, Agent, or Firm*—Buchanan Ingersoll & Rooney PC

(57) ABSTRACT

An insert for use together with an absorbent article such as a nappy, an incontinence product, a sanitary towel, a panty liner or the like. The insert has an first side, a second side and an essentially non-urine-absorbing spacer element adapted to keep a portion of the absorbent article at a distance from the skin of a wearer during use. The insert also includes an essentially non-urine-absorbing liquid-permeable retaining layer located against the spacer element, the retaining layer being capable of retaining feces.

67 Claims, 5 Drawing Sheets

U.S. PATENT DOCUMENTS

| | | | |
|---|---|---|---|
| 6,346,097 B1 * | 2/2002 | Blaney | 604/327 |
| 6,395,955 B1 * | 5/2002 | Roe et al. | 604/361 |
| 6,440,116 B1 | 8/2002 | Tanji et al. | |
| 6,458,111 B1 | 10/2002 | Onishi et al. | |
| 6,595,972 B1 * | 7/2003 | Wise et al. | 604/385.01 |
| 6,716,204 B1 * | 4/2004 | D'Acchioli et al. | 604/385.19 |
| 2002/0082570 A1 | 6/2002 | Mishima et al. | |

FOREIGN PATENT DOCUMENTS

| | | |
|---|---|---|
| EP | 1 064 898 A3 | 1/2001 |
| EP | 1064898 A2 * | 1/2001 |
| EP | 1 097 685 A2 | 5/2001 |
| JP | 07-231904 | 9/1995 |
| JP | 2000-42033 | 2/2000 |
| JP | 2000-333992 | 12/2000 |
| JP | 2001-276125 | 10/2001 |
| JP | 2002-2191631 | 7/2002 |
| WO | WO 9107156 A1 * | 5/1991 |
| WO | 97/17920 | 5/1997 |
| WO | 98/17219 A1 | 4/1998 |
| WO | 98/33463 | 8/1998 |
| WO | 99/07317 A1 | 2/1999 |
| WO | 99/60975 A1 | 12/1999 |
| WO | WO 99/60975 * | 12/1999 |
| WO | 00/00226 A1 | 1/2000 |
| WO | 00/00228 A1 | 1/2000 |
| WO | 00/00232 A1 | 1/2000 |
| WO | 00/00240 A1 | 1/2000 |
| WO | 01/24751 A1 | 4/2001 |
| WO | WO 0124751 A1 * | 4/2001 |

* cited by examiner

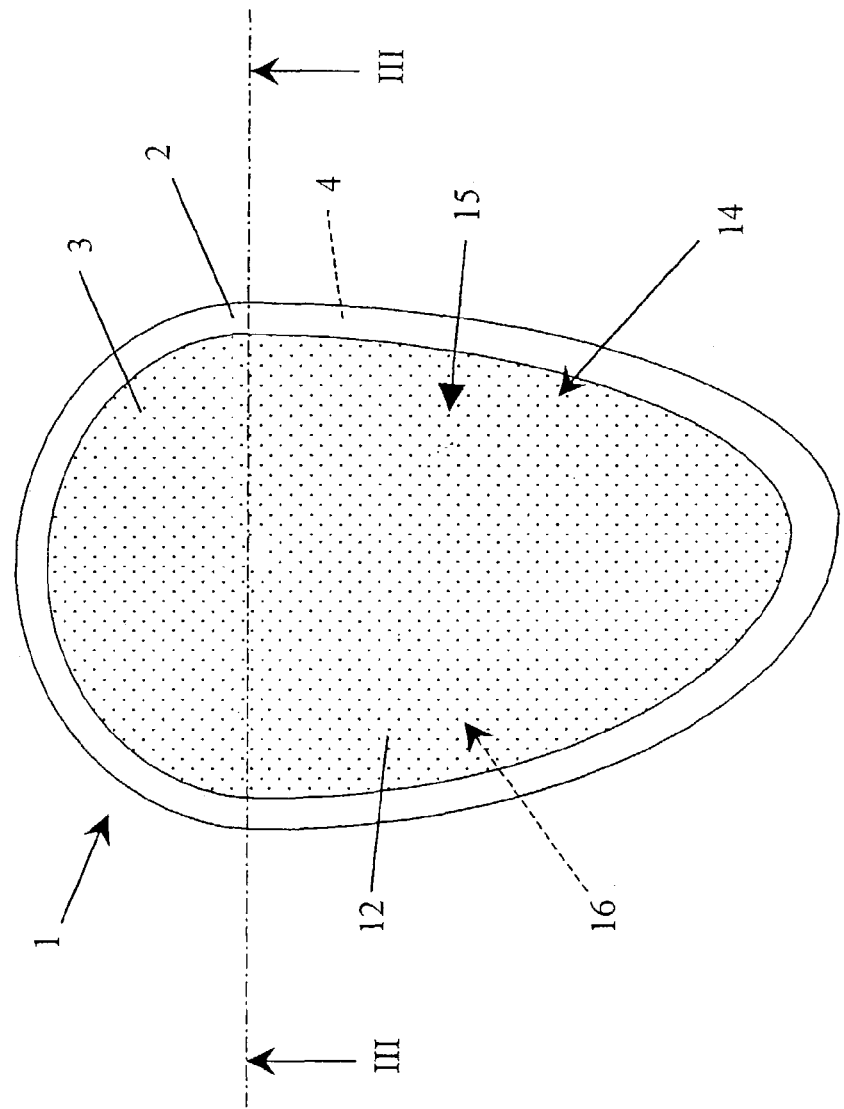

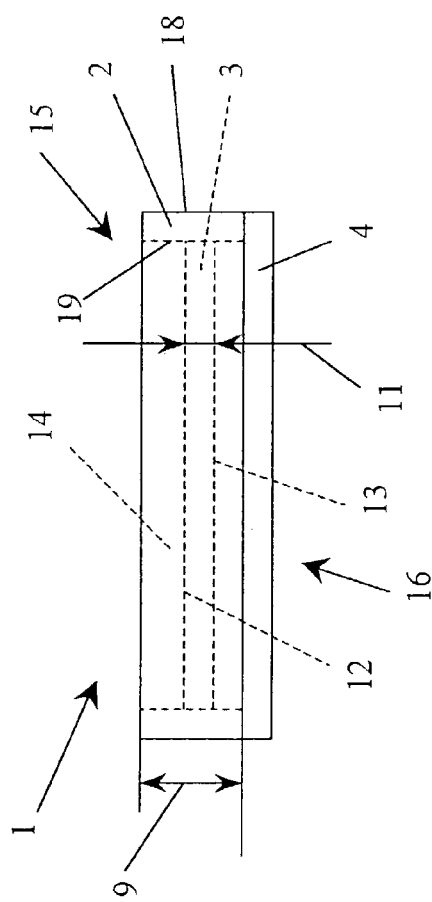
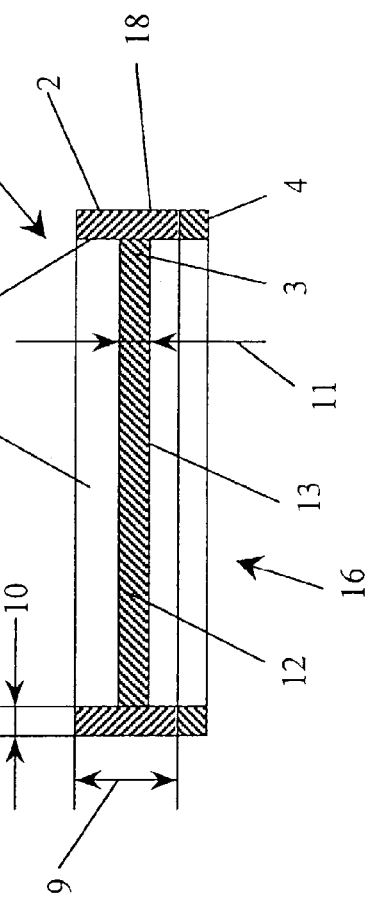

INSERT FOR ABSORBENT ARTICLE HAVING A FECES RETAINING LAYER AND SPACER ELEMENT

CROSS REFERENCE TO RELATED APPLICATIONS

The present application claims priority from U.S. provisional application No. 60/365,818, filed on Mar. 21, 2002.

TECHNICAL FIELD

The present invention relates to an insert for use together with an absorbent article such as a nappy, an incontinence product, a sanitary towel, a panty liner or the like.

BACKGROUND

It has long been known that the long-term use of absorbent articles such as nappies for children and adults can give rise to skin irritation of various types. Skin irritation may originate in chafing on account of mechanical action, or moisture-related problems of various types as a result of the skin of a wearer coming into contact with a moist surface of the absorbent article, or the skin of a wearer coming into contact with bowel movements present in the nappy. In this context, bowel movements or movements mean feces.

As far as bowel movements are concerned, the problem of skin irritation arises especially when movements are mixed with urine, because such a mixture starts known reactions comprising inter alia ammonia, enzymes and a large quantity of bacteria. The mixture of movements and urine moreover affects the skin of a wearer to an especially great extent when the skin is damaged or affected in some other way, for example by chafing or other mechanical action.

The interaction of several factors leads to the development of nappy dermatitis. Moist skin means that chafing and pressure rubs the skin more readily. A higher moisture content also means that penetration of the skin by irritating substances can increase, and also that bacteria and fungi thrive to a greater extent. Occlusion of the skin and the breakdown of the urea in urine into ammonia results in the pH being increased. The higher pH value leads to enzymes (lipases and proteases) originating from the intestine and from microorganisms in the movements being able to break down the skin. This can easily become a vicious circle in which various factors facilitate and intensify one another.

The best way of avoiding dermatitis occurring is by creating circumstances which counteract the factors which create and support the nappy dermatitis process. It is desirable for a wearer to keep the skin as dry as possible, to air the skin frequently and to change wet nappies. Mechanical shear forces should be minimized by choosing materials which are as smooth and soft as possible, and reducing rubbing between the nappy and the skin. By applying a softening protective lotion or cream to the skin, it is also possible to strengthen the barrier against penetration by irritating substances and enzymes. In more serious cases of dermatitis, microorganisms may have infected the damaged skin, and treatment with more active medicaments is required. Use is then made of ointments containing cortisone and various fungicidal and bactericidal agents.

Various ways of solving the abovementioned problems associated with an absorbent article which receives movements and urine have been proposed, inter alia by using various arrangements such as inserts for separating movements from urine, or by using different materials or inserts for transporting liquid away from the interface between the skin and the absorbent article.

WO 99/60975 discloses an absorbent article comprising an arrangement with fairly non-compressible spacer elements which form a zone within which movements are intended to be collected. The non-compressible spacer elements can keep some of the movements present in the zone away from the skin of a wearer, but simply providing a zone in the form of an open "box" allows the movements present in the zone to move freely without any control whatsoever. This results in, for example, the possibility of movements, especially loose movements, moving within the zone in such a manner that they accumulate locally within the zone in such an amount that they come into contact with the skin of a wearer. Furthermore, loose movements can move in the zone on account of the movements of a wearer in such a manner that they can "splash" against the skin of the wearer.

WO 99/07317 discloses an absorbent article comprising an arrangement which swells on contact with liquid and forms a container for movements. One problem of such an arrangement is that it makes great demands of the material in the swelling body and that the functioning of the arrangement depends on it being exposed to a sufficient amount of moisture. Furthermore, the arrangement leads to the same functional problems as WO 99/60975.

WO 98/17219 discloses an absorbent article comprising a fixed arrangement for collecting movements. The arrangement includes a ring made of an elastically compressible material arranged in a central part of the absorbent article. The arrangement is equipped with channels along the perimeter of the arrangement, which allow liquid to migrate out from the area bounded by the arrangement. An arrangement comprising too compressible a material results in problems of the arrangement keeping its shape, and moreover said channels allow a certain amount of liquid movements to run out of the arrangement and thus spread over parts of the nappy which come into contact with the skin.

EP 1064898 discloses an absorbent article, or insert, intended to deal with both urine and movements. The article is constructed from an upper layer with a number of holes, which upper layer is located above a retaining layer for movements, which retaining layer is located above a liquid/moisture-absorbing layer. The retaining layer has a structure with a number of cavities.

The absorbent article has elastically deformable leakage barriers which are intended to fit tightly against the skin of a wearer in order to eliminate side leakage and which surround and define a region where urine and waste products are intended to come to lie. The leakage barriers also define the outer edges of the absorbent article. The various layers mentioned above are located in the region defined by the leakage barriers and against an inner side of the leakage barriers.

The liquid/moisture-absorbing layer is located against the retaining layer in such a manner that a gap arises between the two layers.

The purpose of the gap is that the movements which pass through the retaining layer via the cavities are to be retained in the space defined by the gap.

According to EP 1064898, the cavities have a size which is the same as or larger than the holes which have a size of 20-500 $mm^2$, which means that the majority of the movements pass through the retaining layer to the cavity constituted by the gap.

The EP 1064898 arrangement intended to retain movements is unnecessarily complicated, and the space constituted by the gap can be compressed. The possibility of storing movements is therefore limited. Moreover, the leakage barriers are elastically deformable in such a manner that the possibility exists of the skin of a wearer coming into contact with any movements which have not been transported away from the upper layer.

A desire remains to obtain an absorbent article with an improved capacity for keeping the skin of a wearer free from contact with movements so as to reduce the problem of skin irritation which arises as a result of contact between the skin and the movements/urine.

The previously known absorbent articles which do not separate movements from urine still allow contact between movements present in the absorbent article and the skin of a wearer, which involves a risk of skin irritation. Such articles are characterized by only having good transport of liquid away from the interface between the skin and the absorbent article for the purpose of creating a dry surface of that part of the absorbent article which faces the wearer.

A desire therefore exists to solve the problem with an absorbent article which allows movements and urine to be received but which lessens or completely reduces the contact between the skin and movements when the absorbent article is used.

SUMMARY

Embodiments of the invention are intended to solve the problems indicated above of previously known absorbent articles such as nappies, incontinence products, sanitary towels, panty liners or the like, with a special storage arrangement for movements for use in the absorbent articles. According to embodiments of the invention, such a storage arrangement for movements involves an insert, which insert has an upper side and a lower side. The insert includes an essentially non-urine-absorbing spacer element which keeps the absorbent article at a distance from the skin of a wearer during use.

An insert made according to embodiments of the invention also comprises an essentially non-urine-absorbing liquid-permeable retaining layer located against the spacer element, which retaining layer is capable of retaining movements.

As indicated above, the insert according to some embodiments is intended to be used in an absorbent article. An absorbent article typically comprises a liquid-permeable surface layer which is intended to lie against the skin of a wearer, an absorbent body for absorption of liquid discharged from the wearer, and an impermeable backing. An absorbent article can be described as having, when spread out, a length extent and a width extent in the X direction and the Y direction and a height (thickness) in the Z direction. During use of the insert, the lower side of the insert is preferably located against the surface layer of the absorbent article.

According to one embodiment of the invention, the retaining layer is located inside a structure, which structure is defined and delimited by one or more spacer element(s). The retaining layer is advantageously located in such a manner that the retaining layer lies against the spacer element inside the structure. The spacer element is designed in such a manner that the skin of the wearer is prevented from coming into contact with the retaining layer during use of the insert.

According to this embodiment of the invention, the spacer element, together with the retaining layer, delimits and defines a storage space for movements. The storage space is delimited in its horizontal extent by the spacer element and consists, during use of the insert, of a volume which is delimited by the spacer element, the retaining layer and the skin of the wearer.

The extent of the retaining layer in this embodiment therefore corresponds to an area which is defined by the storage space, that is to say an area which is delimited and defined by the spacer element.

In this embodiment of the invention, the retaining layer is preferably located inside the region which is delimited by the spacer element. The retaining layer is located with the edge parts of the retaining layer against the inner boundary surface of the spacer element. The retaining layer is moreover located against the spacer element at a distance from the lower side of the insert and at a distance from the upper side of the insert. The retaining layer can, for example, be located in the middle of the height of the spacer element, or at another suitable distance from the upper and lower sides of the insert. During use of the insert, the spacer element keeps the retaining layer away from the skin of a wearer, which means that the movements which are retained in the retaining layer are not in contact with the skin of a wearer. During use of the insert according to this embodiment, the spacer element moreover can keep the retaining layer at a distance from the absorbent article, which means that the movements which are retained in the retaining layer are not subjected to capillary forces from the absorbent article. This can be advantageous in certain cases, for example when the absorbent article is of such a nature that it is unsuitable for movements to come into contact with the article.

The storage space is intended to receive urine and movements during use of the insert. The storage space is not intended to store movements or urine temporarily for very long, but is intended only to contain urine and movements within a certain area of extent. The storage space allows a large quantity of urine and movements to be stored for a short time in the storage space at the same time as urine passes through the retaining layer, and movements to be drained and subsequently retained in the structure of the retaining layer, without risk of side leakage.

According to embodiments of the invention, the spacer element or a number of spacer elements can delimit the extent of the storage space in a number of different shapes, for example, saddle-shaped, circular or rectangular. The storage space can also, via a number of spacer elements, be delimited and shaped in such a manner that a number of storage spaces form a grid (matrix) of storage spaces.

According to another embodiment of the invention, the retaining layer is located on the outside of the spacer element structure and against the spacer element. During use of this insert in an absorbent article, the retaining layer is located between the spacer element and the absorbent article.

In this embodiment of the invention, the retaining layer can have an extent which is the same size as the extent of the spacer element. In the context, the extent of the spacer element means the maximum area which can be described by the outermost parts of the spacer element. The spacer element can, for example, have an extent with a bicycle-saddle-shaped geometry, the retaining layer having a corresponding extent with a bicycle-saddle-shaped geometry. In such an embodiment, the retaining layer is applied to the lower side of the spacer element and therefore constitutes the lower side of the insert.

In cases where the spacer element includes a number of spacer elements, the extent of the spacer element means the maximum area which can be described by drawing lines between the outermost parts of the spacer elements.

According to a further embodiment of the invention, the retaining layer has an extent which is greater than the extent of the spacer element(s).

According to the embodiments mentioned above, the retaining layer can therefore have an extent which is the same as or greater than an area which is defined and delimited by the spacer element(s), that is to say the retaining layer can have an extent which is the same as or exceeds the area which can be described by the outermost parts of the spacer element. In cases where the spacer element includes a number of spread-out spacer elements, the wording "outermost parts of the spacer element" means those parts of the spacer element which lie furthest away from one another and which describe the largest area when lines are drawn between said parts of the spacer element.

In other embodiments of the invention, the retaining layer can be located in an arrangement which includes a number of spacer elements in the form of spikes intended to keep the absorbent article at a distance from the skin of a wearer. Such spikes/spacer elements can be located on selected parts of the retaining layer, for example at the periphery of the retaining layer and/or in selected places in the extent of the retaining layer or on the surface of the retaining layer. Spacer elements in the form of spikes can be air bubbles in a suitable material, for example, plastic, foam, non-woven etc.

By arranging the retaining layer according to the embodiments mentioned above, draining of movements is facilitated, and it is made easier for the retaining layer, by virtue of its structure, to retain the movements. The structure of the retaining layer is preferably of reticular type with an open porous structure, which will be described in greater detail below.

"Essentially non-urine-absorbing" means that the component parts of the insert should preferably not retain any urine after wetting has occurred. The retaining layer should suitably transport liquid away, or at least not to any great extent prevent liquid from reaching the absorbent body. In purely practical terms, it is in principle inevitable that a drop or a few drops of liquid will be retained in a fibrous structure on account of the capillary forces which arise in the various cavities and between the fibres. This is not desirable, however, and is minimized by the embodiments of the invention set forth herein.

The insert is intended to be essentially non-urine-absorbing, and this is in order that the pores or holes in the liquid-permeable surface layer should not become obstructed and thus prevent liquid from penetrating into the absorbent core and being absorbed by the core. It should also be possible for liquid to be transported through the surface layer when repeated wetting takes place. On the other hand, the insert is to some extent absorbent because its purpose is to retain feces. The retaining layer can therefore be treated so as to have a suitable hydrophilic property or include a suitable material with suitable hydrophilicity.

In order that the retaining layer does not block the surface layer, it is desired that the retaining layer be liquid-permeable (that is to say that it does not prevent liquid from penetrating through the surface layer) even when it has been subjected to loading. The retaining layer therefore preferably is a material which has low compressibility, for example reticulated foam with an open porous structure. If a reticulated foam is used as the material for the retaining layer, the reticulated foam should have a free volume which is 80-99%, preferably 96-98%, of the total volume of the retaining layer. Tests have shown that it is advantageous to use a reticulated foam with a free volume which has 97% of the total volume of the reticulated foam. The free volume and the properties mentioned of reticulated foam can also be achieved using other materials with a net-like structure; use can be made of, for example, an open wadding structure, which wadding structure is intended to allow urine to pass through and to retain movements.

The retaining layer is therefore to be liquid-permeable in at least one direction, that is to say in the X, Y or Z direction, preferably in all directions. The retaining layer can also be designed so as purely physically to facilitate the penetration of liquid through it, for example by means of cavities in the structure along the liquid-permeable surface layer of the absorbent article, raised or lowered portions in specific zones or other three-dimensional structures. On that surface of the retaining layer which is intended to lie against the absorbent article during use, additional material can also be attached in such a manner that different three-dimensional structures are obtained.

When the wearer has sensitive skin and may get or has rashes, irritation or bedsores, it is important that the surface of the sensitive skin is not subjected to chafing. In addition to the fact that chafing can, purely physically, cause external damage to the skin, chafing also results in the skin becoming more sensitive to other external influences such as movements, urine and the extreme conditions created thereby. Inserts according to embodiments of the invention solve this problem by retaining movements in the insert in such a manner that there is no or little contact between movements and the skin. Furthermore, inserts according to embodiments of the invention are designed in such a manner that the occurrence of chafing is minimal.

After application, the insert is held in position in the absorbent article by being attached to the absorbent article. That surface of the insert which is intended to lie against the absorbent article during use should therefore have as high friction as possible against the absorbent article in order to increase the retaining effect. In order for the surface of the insert to have high friction, it is suitable to use some form of means of attachment or attachment device or structure, for example adhesive material, such as glue or another suitable material. A means of attachment can be applied to all or parts of the insert depending on the design of the insert and the positioning of the retaining layer. The means of attachment can, for example, be arranged along the spacer element(s) or on parts of or along the whole retaining layer.

Another variant for attaching the insert to the absorbent article is to design the retaining layer in such a manner that it is capable of adhering to the absorbent article, for example by means of a touch-and-close fastener-like structure or another suitable three-dimensional structure which adheres to the surface layer of the absorbent article.

In order to make it possible for the skin of the wearer to have as little contact as possible with the movements which are retained in the insert, it is suitable for the insert to maintain its ability to keep its shape when the insert is subjected to pressure, for example by the wearer sitting down. This means that a desired property of the retaining layer is that it has a certain rigidity, that is to say, a certain ability to resist compression.

Another form of insert can include an absorbent material where the absorbent material can advantageously be constructed from a large number of layers of a liquid-permeable material having a number of holes, the various layers being brought together in such a manner that the various holes are displaced in relation to one another, that is to say that the holes are not aligned with one another. By virtue of its displaced holes, the absorbent material has some ability to retain feces at the same time as liquid is transported through the absorbent material. Such an absorbent material can also be used in combination with a retaining layer in the previously described insert and/or in order to completely or partly fill the storage space which is defined by the spacer element and the retaining layer.

It is also possible to use chemical consistency agents in combination with said retaining layer in the previously described insert and/or for use in the storage space which is formed by the spacer element. Chemical consistency agents have different functions depending on chemical substance and area of application. The purpose of some consistency agents is to absorb liquid to produce a jelly-like or solid consistency, which is advantageous in the present invention. Documents WO 00/00226, WO 00/00228, WO 00/00232, WO 00/00240 and U.S. Pat. No. 6,018,093 mention a number of different chemical consistency agents which are suitable for use for the present invention, for example petroleum-based products, salts, amides, hydroxides etc. and derivatives thereof.

In the description of the present invention, terms such as "urine-absorbing" are used. It is therefore beneficial to know what is meant by urine. In Geigy Scientific Tables, Volume 1 (1981), "Units of measurement, Body fluids, Composition of the body & Nutrition", relative viscosities of urine of different composition are listed. The relative viscosity of distilled water=1.00.

The collection of tables mentioned above gives the following relative densities of urine.

| Urine from: | Relative density |
| --- | --- |
| New-born (a few days old) | 1.012 |
| New-born after liquid intake | 1.004 |
| Adult | 1.015 |

Table 6, page 56, in said collection of tables gives the relationship between relative density and relative viscosity:

| Relative density | Relative viscosity |
| --- | --- |
| 1.005 | 1.0 |
| 1.016 | 1.02 |
| 1.022 | 1.09 |
| 1.024 | 1.14 |

The viscosities of urine mentioned above are to be seen as an aid in defining urine to which embodiments of the invention will be subjected. As can be seen, the term urine is a relative term, and the viscosity of urine depends on the composition of the urine. The viscosity can vary depending on illnesses, liquid intake, age, sex, food intake etc. The viscosity increases if the urine contains elevated quantities of protein, blood or leucocytes. The definitions above relating to urine should therefore not be regarded as definitive but as target values as the viscosity of urine can fluctuate depending on a number of factors.

Urine should therefore be understood as liquid which passes through the urethra when a person urinates, and can have a viscosity according to the above-mentioned tables, but may also have both higher or lower viscosity.

Movements mean matter which passes through the anal opening when a person evacuates the bowels and, according to the invention, movements preferably have a higher viscosity than urine.

Depending on the purpose of the embodiments of the present invention, that is to say adult nappies, children's nappies etc., the retaining layer can be adapted to retain more or less viscous movements by virtue of the structure of the retaining layer being changed, for example by means of smaller or more curved through-ducts, or larger or smaller open cells. The retaining layer is therefore preferably intended to retain movements which are liquid.

In another embodiment, the insert includes an absorbent layer located on a lower side of the retaining layer, and a liquid-impervious layer located on a side of the absorbent layer opposite the retaining layer.

In another embodiment, the insert includes an upper side and a lower side opposite the upper side, the upper side intended to face a wearer's skin while being worn, a liquid-permeable and essentially non-urine-absorbent retaining layer capable of retaining bowel movements, and at least one essentially non-urine-absorbent spacer element located against the retaining layer, the at least one spacer element defining the upper side of the insert, the at least one spacer element being arranged to keep the absorbent article at a distance from a wearer's skin, the retaining layer having an outer periphery located against an inner boundary surface of the spacer element, an upper part of the spacer element extending above the upper surface of the retaining layer, and a lower part of the spacer element extending beyond the lower surface of the retaining layer.

In another embodiment, the insert includes an upper side and a lower side opposite the upper side, the upper side intended to face a wearer's skin while being worn, a liquid-permeable and essentially non-urine-absorbent retaining layer capable of retaining bowel movements, and at least one essentially non-urine-absorbent spacer element located against the retaining layer, the at least one spacer element defining the upper side of the insert, the at least one spacer element being arranged to keep the absorbent article at a distance from a wearer's skin, the spacer element having an upper surface located at the upper side of the insert and a lower surface opposite the upper surface, the retaining layer having an upper surface and a lower surface opposite the retaining layer, the lower surface of the spacer element being positioned against the upper surface of the retaining layer.

The embodiments of the invention described above can be combined to form further embodiments.

BRIEF DESCRIPTION OF FIGURES

The invention will be described in greater detail below with reference to the figures shown in the accompanying drawings, in which FIG. 1 shows a view from above of an insert comprising a spacer element and a retaining layer according to one embodiment of the invention, FIG. 2 shows a side view of the insert according to FIG. 1, FIG. 3 shows a view of the section III-III in FIG. 1.

DETAILED DESCRIPTION OF EMBODIMENTS OF THE INVENTION

Figure 4:
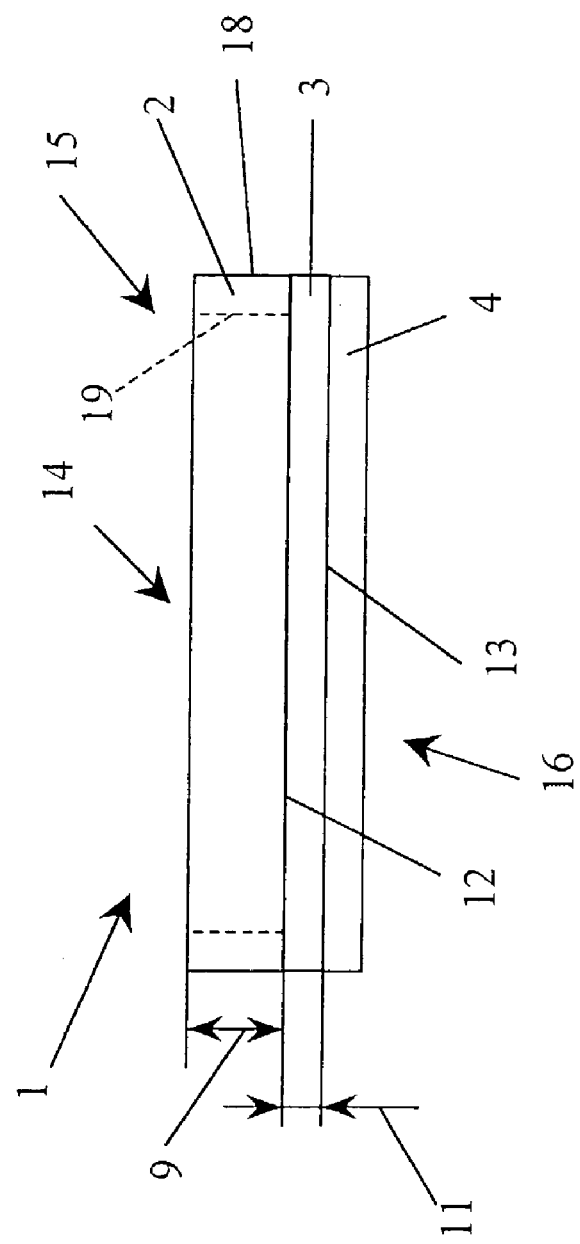
FIG. 4 shows a side view of the insert according to an alternative embodiment.

FIGS. 1-3 show an insert 1 according to a first embodiment of the invention, which insert has an upper or first side 15 and a lower or second side 16, and which insert 1 comprises an essentially non-urine-absorbing spacer element 2. An insert 1 can also comprise an essentially non-urine-absorbing liquid-permeable retaining layer 3 with an upper or first surface 12 and a lower or second surface 13, which retaining layer 3 is capable of retaining movements (feces). The spacer element 2 and the retaining layer define a storage space 14 for movements. It is not necessary that the spacer element 2 bound the insert to form a storage space. A main function of the spacer element 2 is to keep the absorbent article 5 at a distance from the skin of a wearer.

In this description, "extent" relates to a geometrical extent in the X direction and the Y direction as below, and a "thickness" or "height" relates to a geometrical extent in the Z direction.

In FIG. 1, the extent of the spacer element 2 describes a bicycle-saddle shape by means of its outer boundary surface 18. However, the spacer element 2 can have an extent and shape which result in an outer boundary surface which describes, for example, a rectangle or a square.

Figure 5:
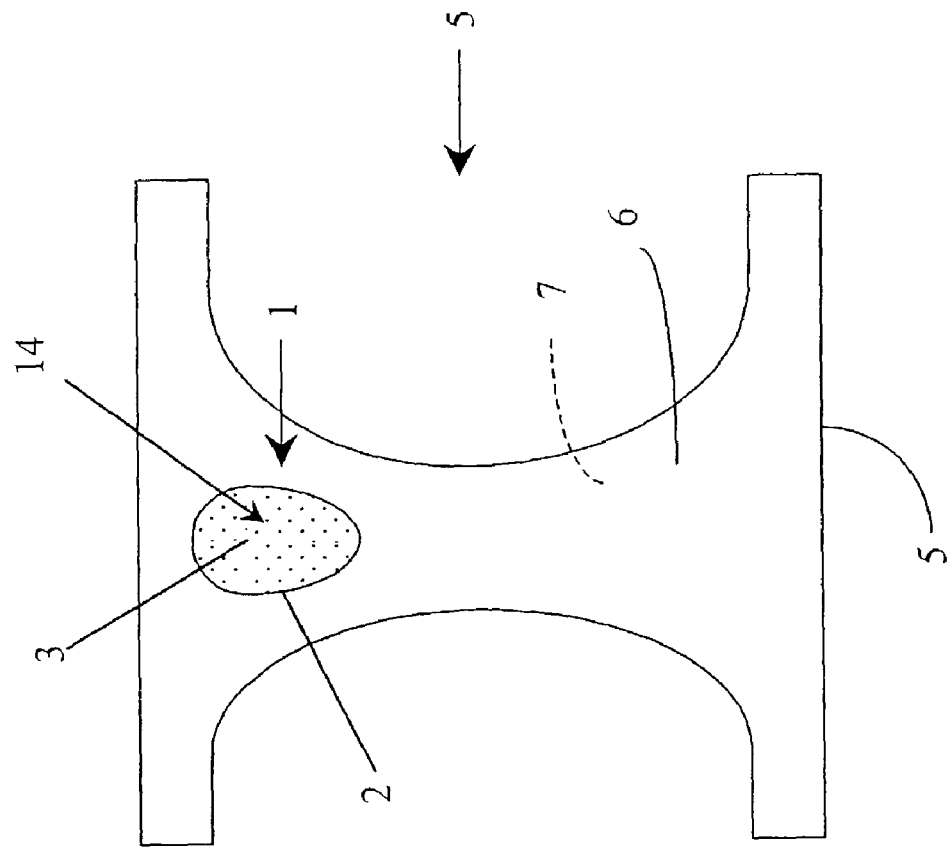
FIG. 5 shows an insert according to FIGS. 1-4 during use together with an absorbent article.
Figure 6:
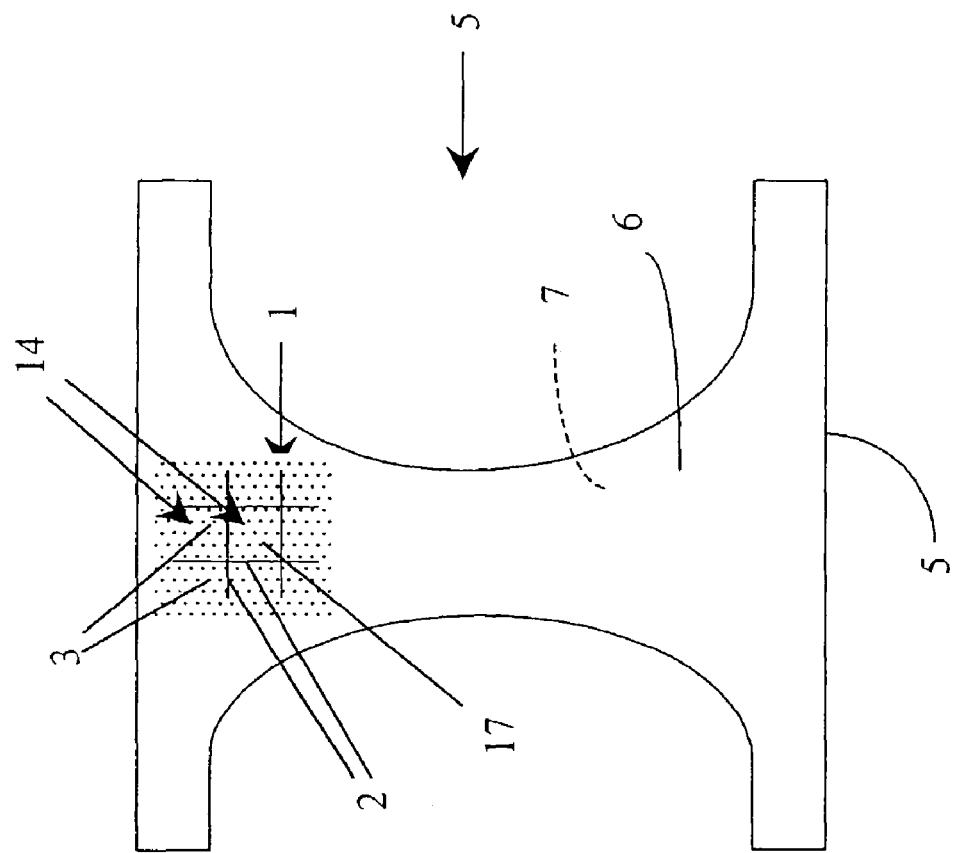
FIG. 6 shows an insert according to a further alternative embodiment during use together with an absorbent article.

The insert is intended to be used in an absorbent article 5 (see FIGS. 5 and 6). An absorbent article 5 typically comprises a liquid-permeable surface layer 6 which is intended to lie against the skin of a wearer, an absorbent body 7 for absorption of liquid discharged from the wearer, and an impermeable backing 8. An absorbent article can be described as having, when spread out, a length extent and a width extent in the X direction and the Y direction (the plane) and a height (thickness) in the Z direction, that is to say that the Z direction extends into the absorbent article at right angles to the length extent and the width extent of the absorbent article when spread out.

During use of the insert 1, the lower side 16 of the insert is located against the surface layer 6 of the absorbent article 5. According to the embodiment shown in FIGS. 1, 2 and 3, this means that the lower side of the spacer element 2 is located against the surface layer of the absorbent article 5.

FIGS. 1-3 show an insert 1 comprising a spacer element 2 and a retaining layer 3 which together have a bicycle-saddle shape, that is to say a two-dimensional pear shape or a "punctured circle" which is wider on one side and narrower on the opposite side. According to FIG. 1, said spacer element 2 has a curved or shaped strip of rectangular cross section with a first height 9 and a first width 10. In other embodiments, the spacer element can have a cross section other than rectangular, for example circular or oval. The retaining layer 3 can have a thickness described by a second height 11.

The spacer element 2 can include a number of sections which, during manufacture of the insert, can be assembled into a suitable shape, for example by gluing or vulcanization. The spacer element can also be made in one piece in a separate process, for example by extrusion or in another suitable manner. During manufacture, the spacer element 2 can also be shaped during application to the absorbent article 5 (FIG. 4), for example by extrusion or injection moulding.

In FIG. 1, the retaining layer 3 is shown located inside the structure which is described by the spacer element 2 with the retaining layer 3 located against the spacer element 2. The retaining layer 3 is located against the spacer element 2 in such a manner that the spacer element 2 keeps the retaining layer 3 at a distance from both the absorbent article and the skin of a wearer. The retaining layer 3 is therefore located at a distance from the surface of the absorbent article 5, which leads to advantages such as capillary forces from the absorbent article 5 not affecting the movements present in the retaining layer 3. The retaining layer 3 is moreover located at a distance from the skin of a wearer, which has obvious advantages in that movements present in the retaining layer 3 do not come into contact with the skin of a wearer.

The retaining layer 3 can be located at different distances from the absorbent article 5. The retaining layer can therefore be located directly adjacent to the absorbent article 5, that is to say against the lower part of the spacer element 2, and also at such a distance that a gap is formed between the surface of the absorbent article 5 and the retaining layer.

It can be seen in FIGS. 1, 2 and 3 that the retaining layer 3 can lie against the inner boundary surface 19 of the spacer element 2 and that the retaining layer 3 has the same extent as the area described by the inner boundary surface 19 of the spacer element 2.

FIG. 2 shows a side view of the insert according to FIG. 1, where the peripheral parts of the retaining layer 3 lie against the inner boundary surface 19 of the spacer element 2. Peripheral parts mean the edges of the retaining layer which bound the extent of the retaining layer in the plane, that is to say in the X and Y directions.

FIG. 3 shows a view of the section III-III in FIG. 1, which shows that the spacer element 2 has a rectangular cross section in the embodiment described. The inner boundary surface 19 of the spacer element 2, which inner boundary surface lies against the peripheral parts of the retaining layer 3, is described by the first height 9. In this embodiment, the peripheral parts of the retaining layer 3 lie against the wider side of the spacer element 2, which wider side, according to this embodiment, is constituted by the height of the spacer element 2. The retaining layer 3 is preferably attached to the spacer element 2 in the position described above.

In other embodiments, the spacer element 2 can have a square cross section or a rectangular cross section, with the narrower side of the spacer element lying against the peripheral parts of the retaining layer 3.

The retaining layer 3 can be attached to the spacer element 2 using any suitable technique, for example gluing, vulcanization, or in another known manner.

In FIGS. 2 and 3, it can be seen that the retaining layer 3 is arranged in the insert 1 in such a manner that the upper surface 12 of the retaining layer 3 is situated at a distance from the upper side 15 of the insert 1 and also that the lower surface 13 of the retaining layer 3 is situated at a distance from the lower side 16 of the insert 1. During use of such an insert in an absorbent article, the spacer element 2 keeps the retaining layer 3 at a distance from both the absorbent article and the skin of a wearer.

FIGS. 2 and 3 also show a means of attachment 4 on the lower side of the spacer element 2. Said means of attachment according to FIG. 3 has an extent which is the same as the width 10 of the spacer element, but the means of attachment can of course be a layer with an extent corresponding to the extent of the insert 1.

FIG. 4 shows an alternative embodiment of the invention where the upper surface 12 of the retaining layer 3 is located on the lower side of the spacer element 2, that is to say on the lower side 16 of the insert. The retaining layer 3 is located against that side of the spacer element 2 which constitutes the first width 10. The upper surface 12 of the retaining layer 3 lies against the narrower side of the spacer element 2. FIG. 4 shows that a means of attachment 4 is arranged on the lower surface 13 of the retaining layer. The means of attachment 4 can, as in the embodiment shown in FIG. 3, have an extent which corresponds to the width 10 of the spacer element 2, but can also be a layer with an extent corresponding to the extent of the insert 1.

FIG. 4 shows that the retaining layer 3 has an extent which is the same as the extent of the spacer element 2, which corresponds to the extent of the insert 1. In the insert 1 according to the embodiment shown in FIG. 4, the means of attachment 4 is located against the lower surface 13 of the retaining layer 3 in such a manner that the means of attachment will lie against the absorbent article 1 during use.

In another embodiment of the invention, the means of attachment 4 can consist of a special design of the retaining layer 3. The means of attachment 4 can be integrated into the retaining layer 3, or the retaining layer 3 can be formed in such a manner that the lower surface 13 of the retaining layer 3 constitutes a means of attachment. Such an integrated means of attachment in the retaining layer 3 can be, for example, spikes or another adhesive structure which is produced during manufacture of the retaining layer 3.

The means of attachment can also be integrated into the spacer element 2 by virtue of the lower side of the spacer element 2 being shaped in a special way, for example during manufacture of the spacer element.

As mentioned above, FIG. 4 shows the retaining layer 3 arranged against the spacer element 2 with the narrower part of the spacer element 2 against the upper surface 13 of the retaining article. In another embodiment of the invention, the spacer element 2 can have a square cross section or a rectangular cross section with the wider side of the spacer element lying against the upper surface 12 of the retaining layer 3.

FIG. 5 shows an insert 1 with a bicycle-saddle shape located in an absorbent article 5. The insert 1 can, for example, be an insert 1 according to any one of the embodiments shown in FIGS. 1-4, located in an absorbent article 5.

A further embodiment of the insert 1 is shown in FIG. 6, which insert 1 comprises a number of spacer elements 2 and a retaining layer 3. The spacer elements 2 together define a rectangular matrix shape comprising rectangular cells 17 each constituting a storage space 14. Some of the rectangular cells are open cells, that is to say, they have a rectangular structure with at least one side removed. The retaining layer 3 can be applied to the spacer elements according to any one of the embodiments indicated above. The retaining layer 3 can therefore be located against the absorbent article with the spacer elements 2 located on the retaining layer 3, according to the embodiment described in FIG. 4. The retaining layer 3 can also consist of a number of retaining layers 3 applied to the spacer elements 2 in a manner as described above according to the embodiments according to FIGS. 2 and 3, that is to say at a distance from the absorbent article 5 and at a distance from the skin of a wearer.

The spacer element 2 and the retaining layer 3 can be a number of different materials; for example, the spacer element 2 and the retaining layer 3 can be a number of layers of non-woven, woven material, film, foam, elastic fabric, or combinations of these. Preferred layer materials for lamination can include polyolefins, for example polyethylene comprising linear low-density polyethylene (LLDPE), low-density polyethylene (LDPE), ultralow-density polyethylene (ULDPE), high-density polyethylene (HDPE), or polypropylene and/or mixtures of these materials.

Several examples of suitable polymer materials which could be used are polyester, polyurethanes, compostable or biodegradable polymers, heat-sensitive polymers, thermoplastic elastomers, metalycene catalyst-based polymers (for example Insite™ available from DOW Chemicals and Exxact™ available from Exxon), and breathable polymers or vapour-permeable (breathable) material.

Fabrics can also consist of or comprise a synthetic fabric, perforated non-woven or film, macroscopically expanded three-dimensional films, foamed materials, filled compositions or laminates and/or combinations thereof. Non-woven material can be manufactured by being spunbond, liquid-perforated, liquid-entangled, carded, air-bonded, calendered or by combinations thereof. According to embodiments of the invention, however, the spacer element 2 and the retaining layer 3 can be essentially non-urine-absorbing (the insert can under certain circumstances retain very small quantities of liquid), and the material of the spacer element and the retaining layer should therefore be formed of a material with suitable hydrophilicity, for example synthetic fibres such as polyolefin fibres which have been treated with wetting agent to the suitable hydrophilicity.

The spacer element 2 and the retaining layer 3 can therefore include a number of different materials.

The spacer element 2 can be a laminate of previously mentioned materials assembled in a number of ways known within the technical field. The spacer element 2 can be laminated/joined together by, for example, thermal bonding, gluing using, for example, spray glue, hot-melt adhesive, latex-based glue or the like, ultrasonic welding, or extruder lamination, which means that a polymer film is laid directly onto a substrate while the film is still in a partly molten state and thus attaches itself to the substrate. This laminate can be one or more layers of elastic plies, preferably compressively elastic and/or non-elastic plies.

The spacer element 2 can also be impregnated and/or coated with a skincare product such as a lotion or the like which lies against the skin of the wearer during use in such a manner that the skincare product is gradually partly transferred to the wearer.

Other characteristics which may be considered desirable in the spacer element 2 are for it to recover its original shape after loading or to be less shapeable in such a manner that the spacer element 2 keeps its shape at least for a while after the loading has begun. It may also be desirable for the spacer element 2 to be sufficiently rigid or pressure-resistant that it is not pressed together completely when it is loaded with a great weight. This is of course in order that, as mentioned previously, the insert will during use function in a retaining manner for the movements present on the retaining layer. It is also preferred that the retaining layer of the insert can receive liquid under a certain load.

The spacer element of rectangular cross section advantageously has a first height 9 of 0.1-3 cm and a first width 10 of 0.1-4 cm. The length/width ratio should be such that the spacer element is not deformed in an undesirable manner during use, for example on account of the spacer element being so high in relation to its width that it bends. The first length and the first width can also be both larger or smaller than indicated above, depending on the size of the absorbent article and the shape of the body of the wearer.

As mentioned, the retaining layer 3 can have a number of different designs. The second height 11 of the retaining layer 3 can, for example, be smaller, larger or alternatively the same size as the first height 9 of said spacer element 2. The retaining layer advantageously has a second height 11 of 0.1-2.0 cm, depending on inter alia the calculated quantity of movements to be received and retained in the structure of the retaining layer. The second height 11 of the retaining layer 3 can also be different in different places on the retaining layer 3, that is to say there can be a certain three-dimensional structure. As it is desirable for the material of the retaining layer 3 to be air-permeable and liquid-permeable, especially adjacent to the liquid-permeable surface layer of an absorbent article, three-dimensional structures can facilitate this, for example by ducts or the like running parallel to the liquid-permeable surface layer of the absorbent article. Three-dimensional structures may also be suitable for retaining movements on the retaining layer 3, for example in the storage space 14, 17.

As in FIG. 6, the insert can have a rectangular shape, but it is also possible within the scope of the invention for the insert to have a different shape, such as a triangular or polygonal shape, oval, circular, rhombic, irregular or similar shape. The insert can also have the shape of a vehicle, house, plant, figure or any other shape which may be considered desirable.

The spacer element 2 is not limited to a particular structure but can be designed as desired. The spacer element can define a storage space for feces, in which storage space 14 the retaining layer 3 can be located. Other absorbent articles can also be located in the storage space in combination with the retaining layer. The spacer element can moreover be H-shaped with two partly defined storage spaces or diamond-shaped with a number of defined storage spaces and a number of partly defined storage spaces. The spacer element 2 can furthermore constitute an open structure which does not define a storage space. The retaining layer 3 can then constitute a boundary to the extent of the area of the insert 1. The spacer element can consist of, for example, a number of spikes, which spikes are attached to the retaining layer 3.

The size of the insert can be varied; for example, the upper side of the insert can have a surface area of roughly 2-500 cm$^2$, preferably 40-350 cm$^2$, most preferably 80-200 cm$^2$. If required, the size of the insert can be adapted to the type of treatment desired, the person who is to use the insert, and the type and size of the absorbent article. There may also be production-related advantages associated with designing the insert in a specific manner, for example in order to minimize waste during manufacture of the insert.

The shape of the insert can be varied depending on where it is intended to fitted on the wearer. As it is within the scope of the invention for the insert to be located anywhere on the absorbent article, it may be important for the insert to be available in different sizes and shapes. A general rule of thumb should be to use large inserts for large areas or large wearers and small inserts for small areas and small wearers, or alternatively a number of smaller inserts for a large area or wearer. Area means the area where movements may be expected to come to lie.

The above description is not to be considered as limiting the invention to use together with only such absorbent articles as just referred to above, but all forms of absorbent article known to an expert in the field of nappies, incontinence products, sanitary towels, panty liners or the like are to be regarded as being included.

A number of possible materials suitable for the retaining layer were discussed above. In order further to illustrate suitable materials, an experiment will be described below, which relates to a material for the retaining layer 3 consisting of a reticulated foam.

A reticulated foam has low compressibility with an open porous structure. If a reticulated foam is used as the material for the retaining layer, the reticulated foam should have a free volume which is 90-99% of the total volume of the retaining layer, that is to say the total volume of the foam. Tests have shown it to be advantageous to use a reticulated foam with a free volume which is 96-98% of the total volume of the reticulated foam, preferably 97% of the total volume of the reticulated foam.

One type of reticulated foam is BULPREN® S, which is a reticulated foam made of polyurethane (polyester-based). Reticulated means a net-like cellular structure where the cellular structure is completely open and does not include any closed cells. BULPREN® S is a standardized filter foam with a density of 30 kg/m$^3$.

Owing to the fact that BULPREN® S has a calibrated cell size, the homogeneous cellular structure and the three-dimensional network of the foam has an ideal filtering capability. Moreover, the foam can be shaken, washed and rinsed a number of times, which means that BULPREN® S allows reuse on a number of occasions.

The insert according to the invention is intended mainly for disposable application but can, by appropriate material selection, also be reusable. It is furthermore possible to impregnate BULPREN® S with a number of special products in order to obtain the desired properties.

BULPREN® S has a free volume corresponding to 97% of the total volume of the reticulated foam.

Experiment

A commercially known absorbent body was used for the experiment, and the experiment was carried out on the commercially known absorbent body and also on the commercially known absorbent body when the latter was coated with the test material mentioned below.

The experiment was performed by the test material being covered by a sheet of rigid plastic-coated cardboard with a centrally located round hole and with a weight of 12 grams. The size of the hole was 3 cm in diameter.

A plastic tube with an inner diameter of 4 cm was located over the hole.

The sheet together with the plastic tube was made to apply a pressure of roughly 100-120 grams to the test material.

The pipe was provided with a cylinder with a weight of roughly 50 grams. The size of the cylinder was adapted to the tube in such a manner that the cylinder could easily slide up and down.

All the component test materials were weighed individually and together, before and after testing.

25 grams of test liquid were placed in the tube, and the cylinder was placed carefully on top of the test liquid.

The size of the cylinder prevented the test liquid being forced up between the cylinder and the tube.

After roughly 10 minutes, the tube with the remaining test liquid and the cylinder were removed as carefully as possible.

Surplus test liquid was scraped away from the test material very carefully.

The diameter of the mark made by the test liquid in/on the test piece was measured, after which its area was calculated.

The basic capacity of the test material was calculated in g test liquid/cm$^2$.

The capacity of the test material per g test material was therefore also calculated in g test liquid/g test material.

The material tested was Bulpren® S 10, both pure and after the material had been impregnated with hydrophilic wetting agent which was allowed to dry in. Hydrophilic wetting agent which has dried in produces a hydrophilic effect.

"g" stands for grams below.

Viscous Liquid:

Feclone™ 13-Brown 20 g dry mix+145 g water, otherwise as per instructions from SiliCloone Studio.

On measurement of the viscosity, using a Brookfield viscometer with spindle no. 4, at 60 rpm and at room temperature (22-23° C.), a viscosity of 4800 mPas was measured.

Laboratory Climate:
roughly 23° C. ambient air temperature and 50% RH.
Sample Size:

10×10 cm

Result

| Test material | Reference | Bulpren S 10 | Bulpren S 10 hydrophilic |
|---|---|---|---|
| Total test liquid uptake (g) | 0.41 | 6.49 | 8.43 |
| Mark size (cm$^2$) | X | 9.6 | 9.6 |
| Material capacity (g/g) | Y | 33.8 | 43.9 |

X and Y not calculated when the test liquid was for the most part lying on the surface.

The invention is not limited to what has been indicated above but can within the scope of the accompanying claims take the form of a number of embodiments. For example, the insert can be positioned in a design arranged in a special way in the absorbent article.

Such an example is for an absorbent body present in the absorbent article to be adapted to receive the insert by virtue of a part of said absorbent body being removed in an extent corresponding to the width extent of the insert. In such cases, the insert can lie directly against an impermeable backing present in the absorbent article, or against the surface layer when the surface layer lies against the impermeable backing as a result of the absorbent body having been removed in that part of the absorbent article where the insert is to be located (the surface layer normally covers the absorbent article with the same extent as the backing and therefore also covers the entire absorbent body even if a "hole" is made therein). The spacer element of the insert then lies against the backing/surface layer in the width direction and against the absorbent body in the height direction. The insert can of course be located against the surface layer in a standard nappy, or similar absorbent articles, where no changes have been made, but the absorbent body lies under the surface layer which is covered by the insert. The insert can therefore be located in a freely selected position in an absorbent article or in a suitable garment.

The insert can also be supplemented with an absorbent body for liquid and an impermeable layer so that it is possible to use the insert in garments which do not have an absorbent body or impermeable layer.

The embodiments of the invention described above can be combined to form further embodiments.

Although only preferred embodiments are specifically illustrated and described herein, it will be appreciated that many modifications and variations of the present invention are possible in light of the above teachings and within the purview of the appended claims without departing from the spirit and intended scope of the invention.

The invention claimed is:

1. An insert for use with an absorbent article, the insert comprising:
   a first side and a second side opposite the first side, the first side adapted to face a wearer's skin while being worn;
   a liquid-permeable and essentially non-urine-absorbent retaining layer capable of retaining bowel movements,
   at least one essentially non-urine-absorbent spacer element located against the retaining layer, the at least one spacer element defining the first side of the insert, the at least one spacer element being arranged to keep a portion of the absorbent article at a distance from a wearer's skin,
   wherein the at least one spacer element and the retaining layer define at least one storage space for bowel movements, the at least one storage space being bounded in a horizontal extent by the at least one spacer element and in a vertical extent by the retaining layer,
   wherein the at least one storage space is open towards the first side of the insert.

2. The insert according to claim 1, the absorbent article being a diaper, an incontinence product, a sanitary towel, or a panty liner.

3. The insert according to claim 1, the second side facing the absorbent article during use.

4. The insert according to claim 1, wherein the retaining layer has an attachment structure for adhering the retaining layer to the absorbent article.

5. The insert according to claim 1, wherein the storage space bounded by the spacer element is bicycle-seat-shaped.

6. The insert according to claim 1, wherein the storage space is rectangular.

7. The insert according to claim 1, wherein the at least one spacer element defines a grid of rectangular storage spaces.

8. The insert according to claim 1, further comprising:
   a chemical consistency agent.

9. The insert according to claim 1, wherein the at least one storage space has a continuous boundary in the horizontal extent such that the at least one storage space is closed in the horizontal extent.

10. The insert according to claim 1, wherein the at least one spacer element has an attachment structure for adhering the spacer element to the absorbent article.

11. The insert according to claim 10, wherein the at least one spacer element has a rectangular cross section.

12. The insert according to claim 10, wherein the storage space bounded by the spacer element is bicycle-seat-shaped.

13. The insert according to claim 10, wherein the storage space is rectangular.

14. The insert according to claim 10, wherein the at least one spacer element defines a grid of storage spaces.

15. The insert according to claim 10, further comprising:
   a chemical consistency agent.

16. The insert according to claim 10, further comprising:
   a liquid-permeable absorbent material.

17. The insert according to claim 10, wherein the retaining layer comprises a reticulated foam.

18. The insert according to claim 10, the retaining layer being hydrophilic.

19. The insert according to claim 10, wherein the attachment structure is an adhesive.

20. The insert according to claim 10, wherein the retaining layer has a free volume which is between about 80% and about 99% of a total volume of the retaining layer.

21. The insert according to claim 20, wherein free volume is between about 96% and about 99% of the total volume of the retaining layer.

22. The insert according to claim 1, wherein the at least one spacer element has a rectangular cross section.

23. The insert according to claim 22, wherein the storage space is bounded by the spacer element is bicycle-seat-shaped.

24. The insert according to claim 22, wherein the storage space is rectangular.

25. The insert according to claim 22, wherein the at least one spacer element defines a grid of storage spaces.

26. The insert according to claim 22, further comprising:
   a chemical consistency agent.

27. The insert according to claim 22, further comprising:
   a liquid-permeable absorbent material.

28. The insert according to claim 22, wherein the retaining layer comprises a reticulated foam.

29. The insert according to claim 22, the retaining layer being hydrophilic.

30. The insert according to claim 22, wherein the retaining layer has a free volume which is between about 80% and about 99% of a total volume of the retaining layer.

31. The insert according to claim 22, wherein the free volume is between about 96% and about 99% of the total volume of the retaining layer.

32. The insert according to claim 1, further comprising:
a liquid-permeable absorbent material.

33. The insert according to claim 32, the retaining layer being hydrophilic.

34. The insert according to claim 32, wherein the retaining layer has a free volume which is between about 80% and about 99% of a total volume of the retaining layer.

35. The insert according to claim 34, wherein the free volume is between about 96% and about 99% of the total volume of the retaining layer.

36. The insert according to claim 1, wherein the retaining layer comprises a reticulated foam.

37. The insert according to claim 36, the retaining layer being hydrophilic.

38. The insert according to claim 36, wherein the retaining layer has a free volume which is between about 80% and about 99% of a total volume of the retaining layer.

39. The insert according to claim 37, wherein the free volume is between about 96% and about 99% of the total volume of the retaining layer.

40. The insert according to claim 1, the retaining layer being hydrophilic.

41. The insert according to claim 40, wherein the retaining layer has a free volume which is between about 80% and about 99% of a total volume of the retaining layer.

42. The insert according to claim 41, wherein the free volume is between about 96% and about 99% of the total volume of the retaining layer.

43. The insert according to claim 1, wherein the retaining layer has a free volume which is between about 80% and about 99% of a total volume of the retaining layer.

44. The insert according to claim 43, wherein the free volume is between about 96% and about 99% of the total volume of the retaining layer.

45. The insert according to claim 1, the retaining layer having an extent which is equal to an area defined by the at least one spacer element.

46. The insert according to claim 45, wherein the retaining layer has an attachment structure for adhering the retaining layer to the absorbent article.

47. The insert according to claim 45, wherein the at least one spacer element has a rectangular cross section.

48. The insert according to claim 45, wherein the storage space bounded by the spacer element is bicycle-seat-shaped.

49. The insert according to claim 45, wherein the storage space is rectangular.

50. The insert according to claim 45, wherein the at least one spacer element defines a grid of rectangular storage spaces.

51. The insert according to claim 45, further comprising:
a chemical consistency agent.

52. The insert according to claim 45, further comprising:
a liquid-permeable absorbent material.

53. The insert according to claim 45, wherein the retaining layer comprises a reticulated foam.

54. The insert according to claim 45, the retaining layer being hydrophilic.

55. The insert according to claim 45, wherein the retaining layer has a free volume which is between about 80% and about 99% of a total volume of the retaining layer.

56. The insert according to claim 55, wherein the free volume is between about 96% and about 99% of the total volume of the retaining layer.

57. The insert according to claim 1, the retaining layer having an extent which is equal to or greater than an area defined by the at least one spacer element.

58. The insert according to claim 57, wherein the at least one spacer element has a rectangular cross section.

59. The insert according to claim 57, wherein the storage space bounded by the at least one spacer element is bicycle-seat-shaped.

60. The insert according to claim 57, wherein the storage space bounded by the at least one spacer element is rectangular.

61. The insert according to claim 57, wherein the at least one spacer element defines a grid of storage spaces.

62. The insert according to claim 57, further comprising:
a chemical consistency agent.

63. The insert according to claim 57, further comprising:
a liquid-permeable absorbent material.

64. The insert according to claim 57, wherein the retaining layer comprises a reticulated foam.

65. The insert according to claim 57, the retaining layer being hydrophilic.

66. The insert according to claim 57, wherein the retaining layer has a free volume which is between about 80% and about 99% of a total volume of the retaining layer.

67. The insert according to claim 66, wherein the free volume is between about 96% and about 99% of the total volume of the retaining layer.

* * * * *